(12) United States Patent
Nakao

(10) Patent No.: US 10,722,144 B2
(45) Date of Patent: Jul. 28, 2020

(54) INFORMATION PROCESSING APPARATUS, INFORMATION PROCESSING SYSTEM, AND INSOLE

(71) Applicant: SONY CORPORATION, Tokyo (JP)

(72) Inventor: Takashi Nakao, Tokyo (JP)

(73) Assignee: SONY CORPORATION, Tokyo (JP)

( * ) Notice: Subject to any disclaimer, the term of this patent is extended or adjusted under 35 U.S.C. 154(b) by 219 days.

(21) Appl. No.: 15/558,278

(22) PCT Filed: May 12, 2016

(86) PCT No.: PCT/JP2016/002334
§ 371 (c)(1),
(2) Date: Sep. 14, 2017

(87) PCT Pub. No.: WO2016/199350
PCT Pub. Date: Dec. 15, 2016

(65) Prior Publication Data
US 2018/0055415 A1    Mar. 1, 2018

(30) Foreign Application Priority Data
Jun. 12, 2015    (JP) .................................. 2015-118931

(51) Int. Cl.
*A61B 5/22* (2006.01)
*G16H 50/30* (2018.01)
(Continued)

(52) U.S. Cl.
CPC ............ *A61B 5/1036* (2013.01); *A61B 5/224* (2013.01); *A61B 5/486* (2013.01); *A61B 5/6807* (2013.01); *A61B 5/6829* (2013.01); *A61B 5/743* (2013.01); *A61B 5/7405* (2013.01); *A61B 5/7455* (2013.01); *A61B 5/7475* (2013.01); *G16H 20/30* (2018.01); *G16H 40/63* (2018.01);
(Continued)

(58) Field of Classification Search
CPC ....... A61B 5/1036; A61B 5/224; A61B 5/486; A61B 5/6807; A61B 5/6829; A61B 5/7405; A61B 5/743; A61B 5/7455; A61B 5/7475; A61B 2562/0247; A61B 2562/04; A61B 2562/046; A61B 2562/164; G16H 20/30; G16H 50/30; G16H 50/20; G16H 40/63; G16H 10/60; G01L 1/16; G01L 1/20; G01L 1/205; G06F 19/3418
USPC ................................................. 600/592, 587
See application file for complete search history.

(56) References Cited

U.S. PATENT DOCUMENTS 6,273,863 B1    8/2001  Avni et al.
7,771,371 B2 *  8/2010  Avni ..................... G01L 5/008
                                                    600/592
(Continued)

FOREIGN PATENT DOCUMENTS

JP          2005-532138 A        10/2005
WO       WO 01/036051 A2         5/2001
WO       WO-0136051 A2 *         5/2001 ............. A61B 5/486

*Primary Examiner* — Navin Natinthithadha
(74) *Attorney, Agent, or Firm* — Paratus Law Group, PLLC

(57) ABSTRACT

An information processing apparatus including circuitry configured to acquire weight distribution information of a subject by at least one sensor, analyze the acquired weight distribution information, and initiate a providing of feedback information based on the analyzed weight distribution information.

22 Claims, 10 Drawing Sheets

(51) Int. Cl.
    *G16H 20/30*     (2018.01)
    *G16H 50/20*     (2018.01)
    *G16H 40/63*     (2018.01)
    *G16H 10/60*     (2018.01)
    *G01L 1/16*     (2006.01)
    *G01L 1/20*     (2006.01)
    *A61B 5/103*     (2006.01)
    *A61B 5/00*     (2006.01)
    *G06F 19/00*     (2018.01)

(52) U.S. Cl.
CPC ............. *G16H 50/20* (2018.01); *G16H 50/30* (2018.01); *A61B 2562/0247* (2013.01); *A61B 2562/04* (2013.01); *A61B 2562/046* (2013.01); *A61B 2562/164* (2013.01); *G01L 1/16* (2013.01); *G01L 1/20* (2013.01); *G01L 1/205* (2013.01); *G06F 19/3418* (2013.01); *G16H 10/60* (2018.01)

(56) References Cited

U.S. PATENT DOCUMENTS

| | | | |
|---|---|---|---|
| 7,998,092 B2 * | 8/2011 | Avni | A61B 5/1036 600/587 |
| 2006/0282017 A1 | 12/2006 | Avni et al. | |
| 2008/0108913 A1 | 5/2008 | Lengsfeld et al. | |
| 2008/0167580 A1 * | 7/2008 | Avni | A43B 3/0005 600/587 |
| 2009/0293319 A1 | 12/2009 | Avni | |
| 2013/0103416 A1 | 4/2013 | Amigo et al. | |
| 2015/0130619 A1 | 5/2015 | Oddsson et al. | |
| 2016/0321947 A1 * | 11/2016 | Toronto | G09B 5/04 |

\* cited by examiner

[Fig. 1]
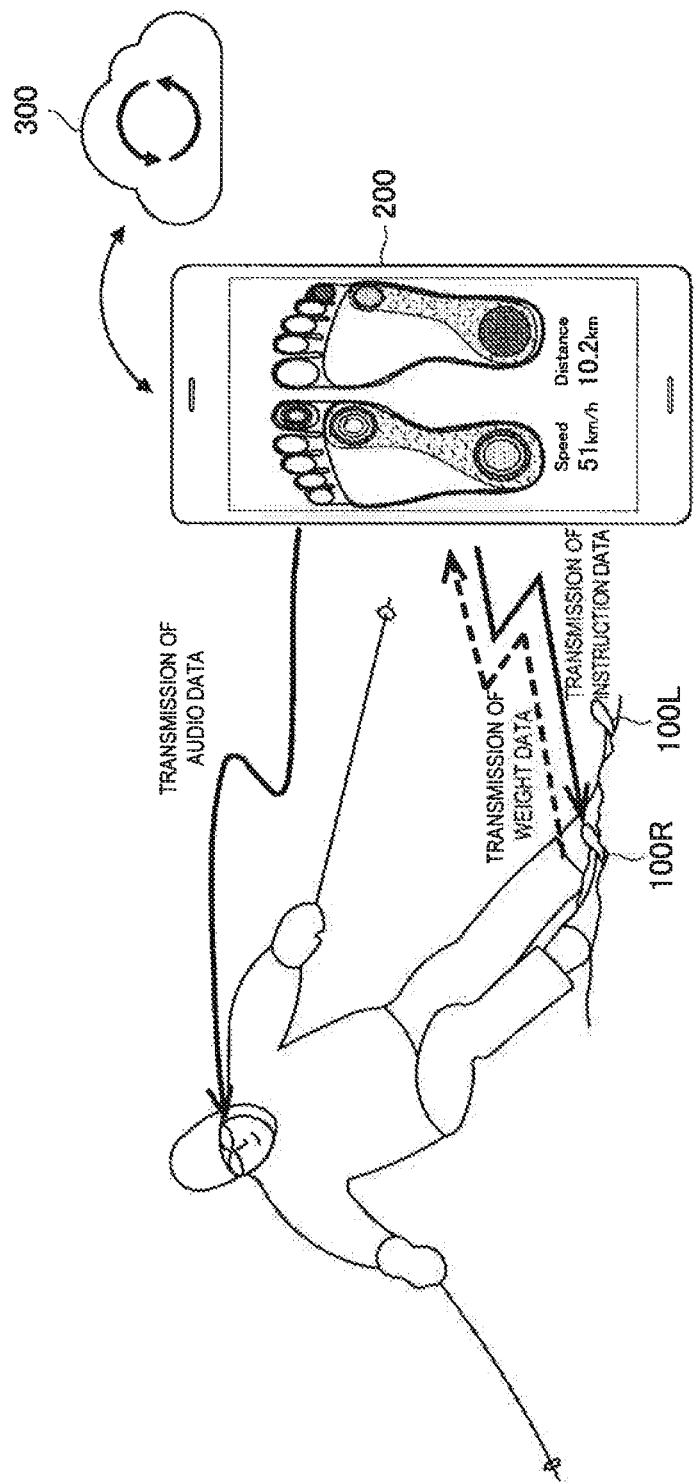

[Fig. 2]
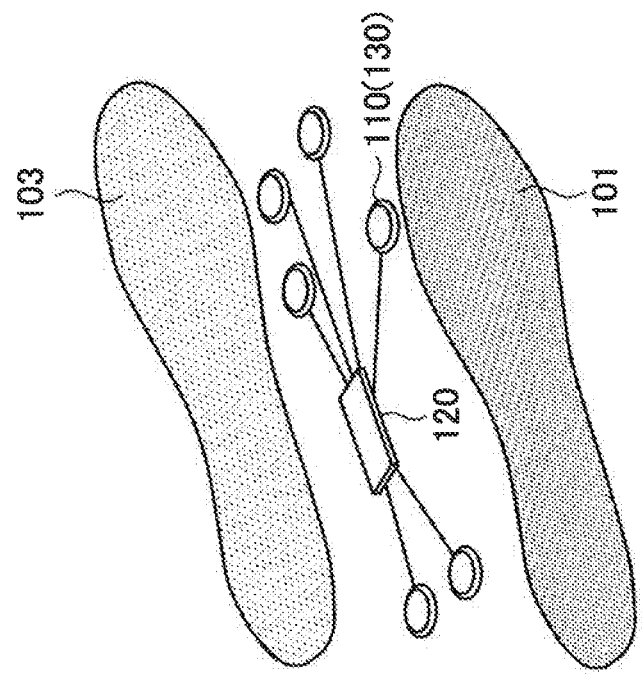
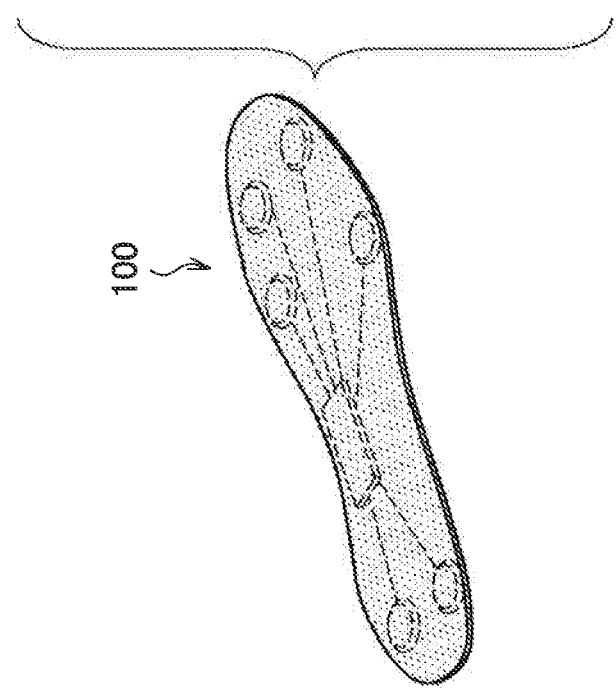

[Fig. 3]
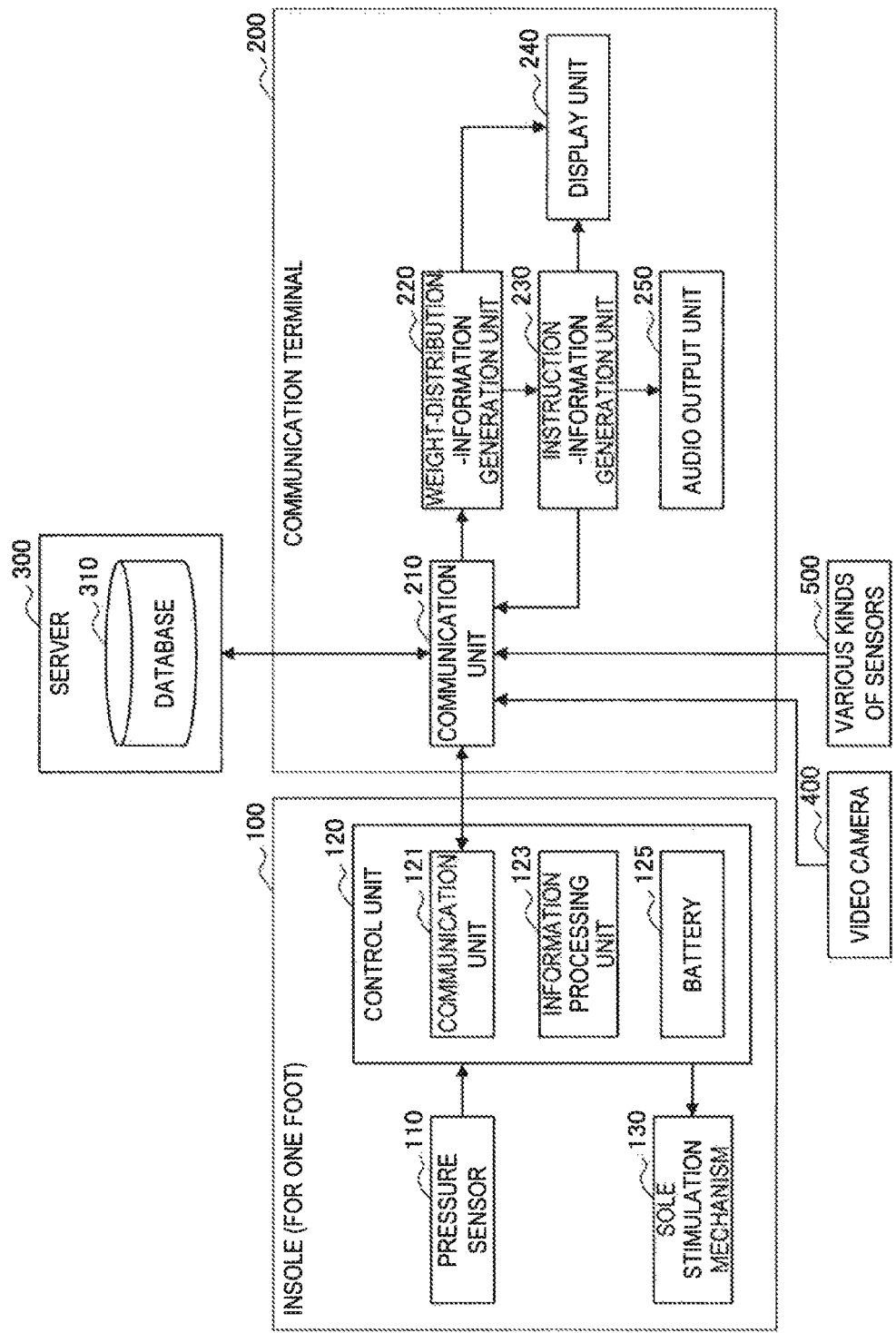

[Fig. 4]
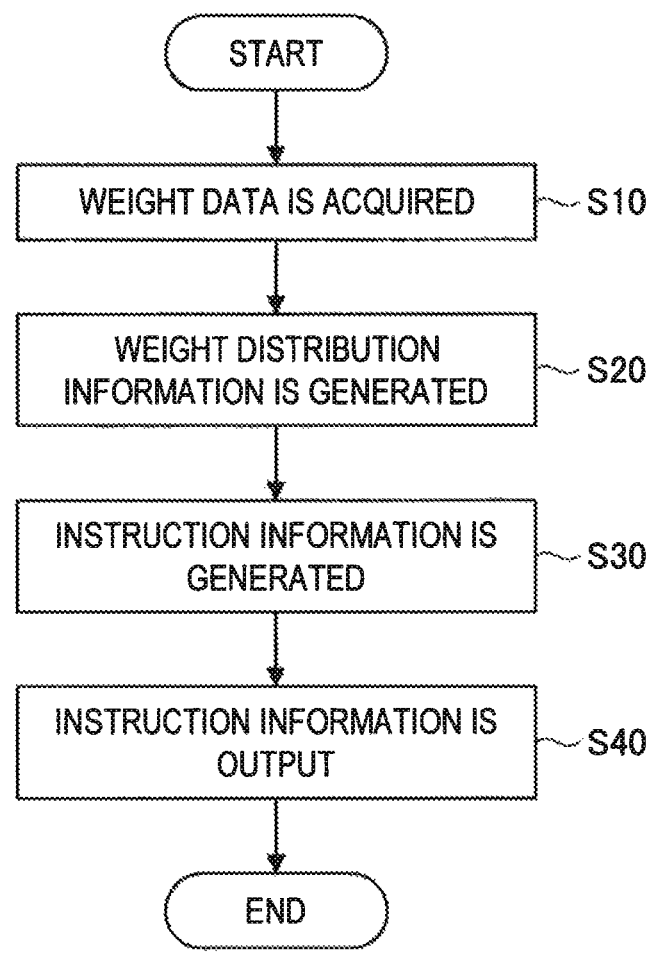

[Fig. 5]
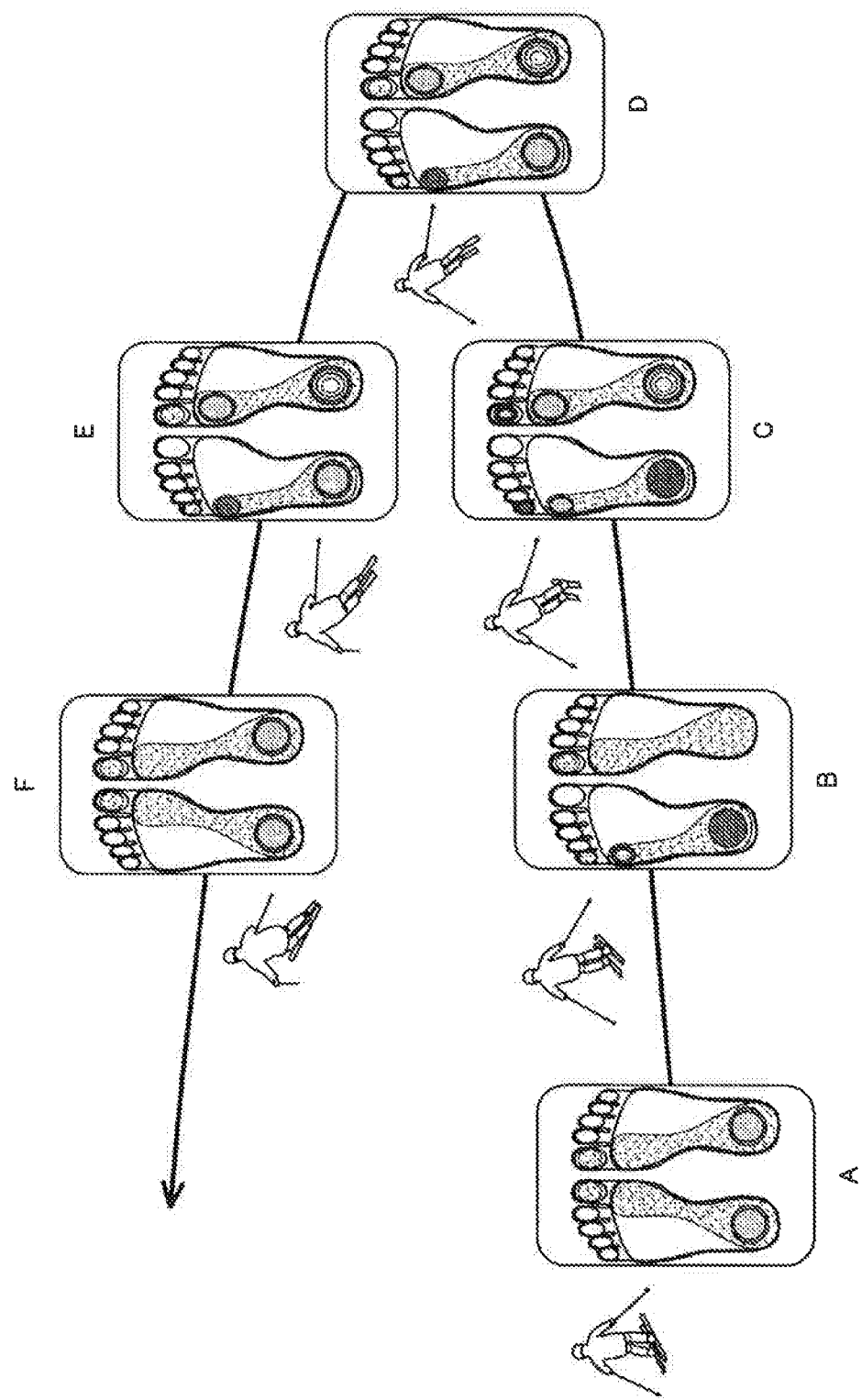

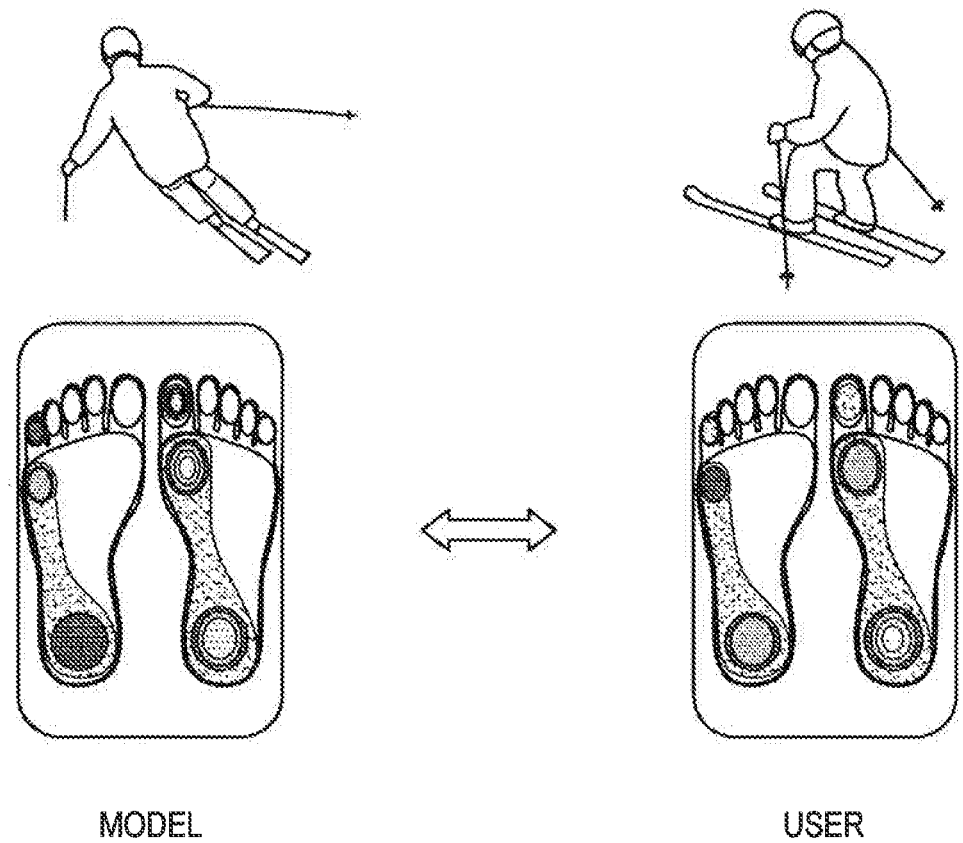
[Fig. 6]
MODEL USER

[Fig. 7]
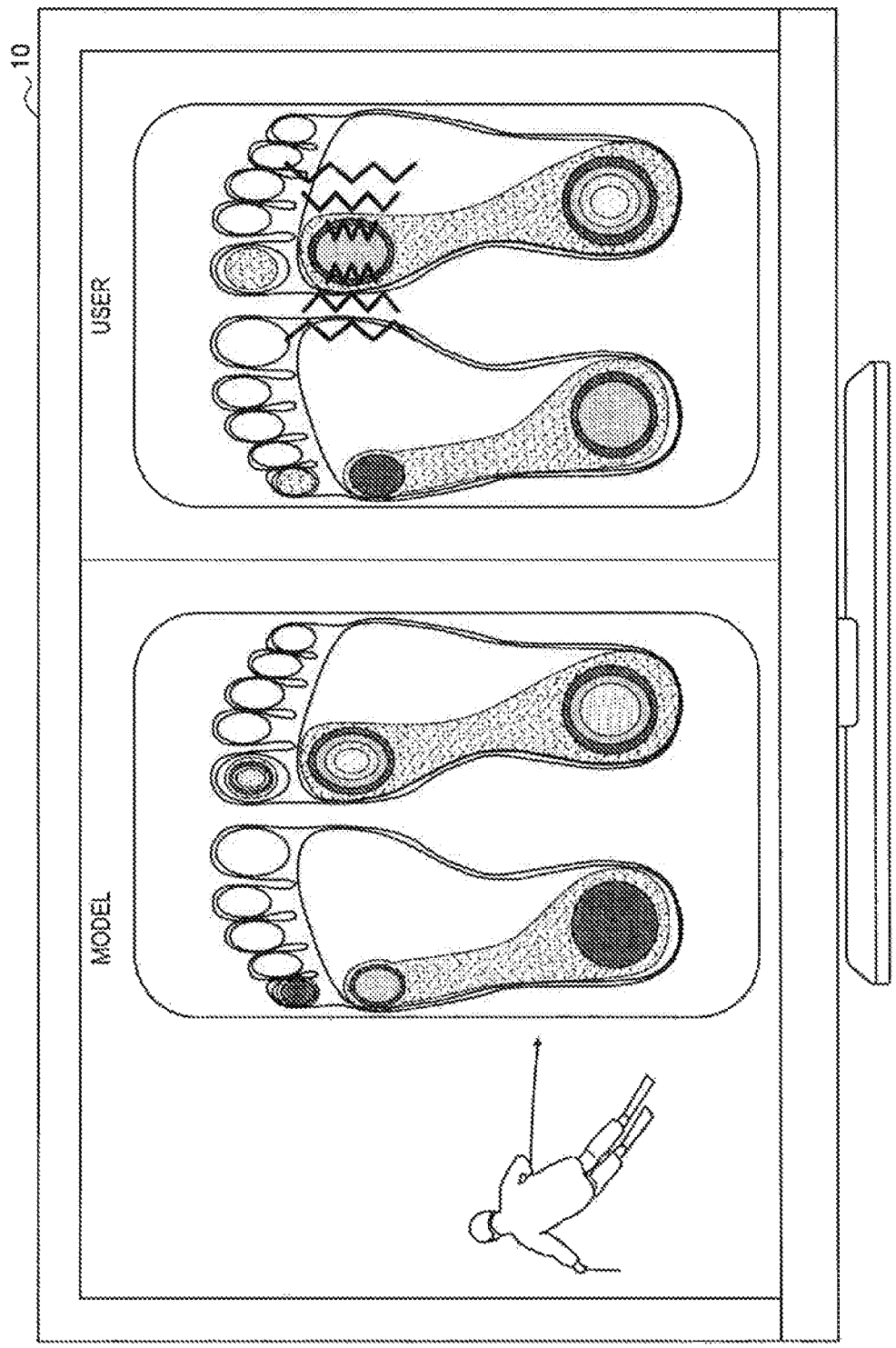

[Fig. 8]
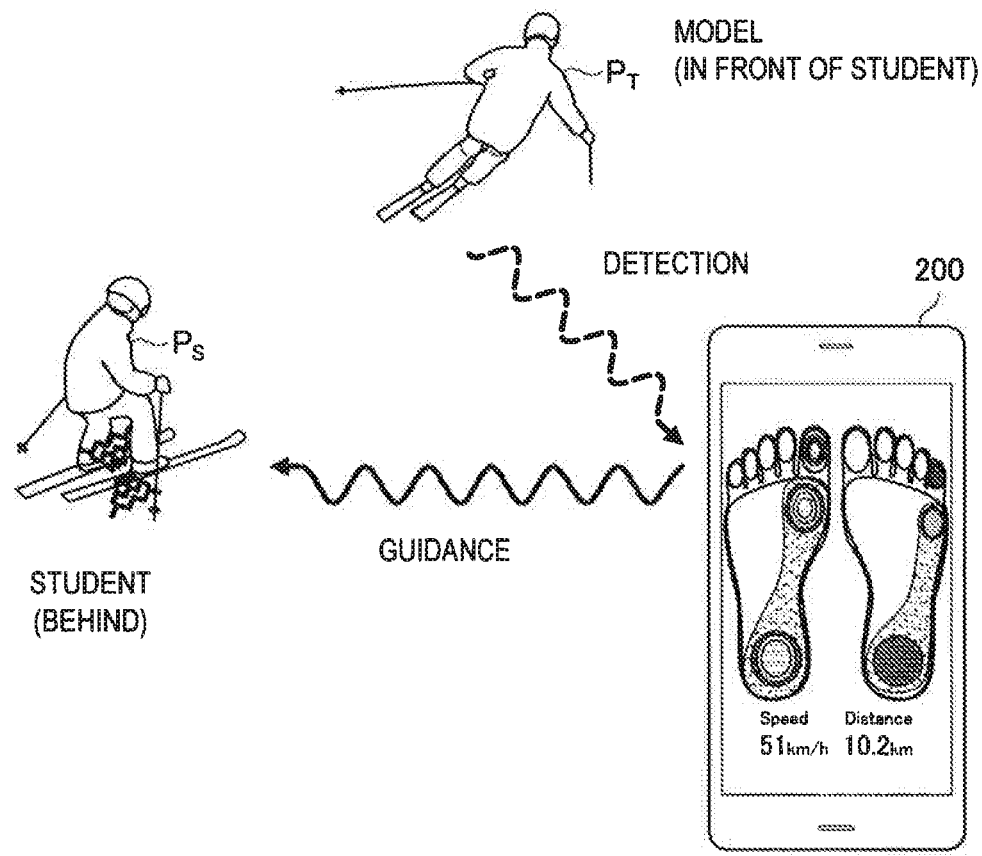

[Fig. 9]
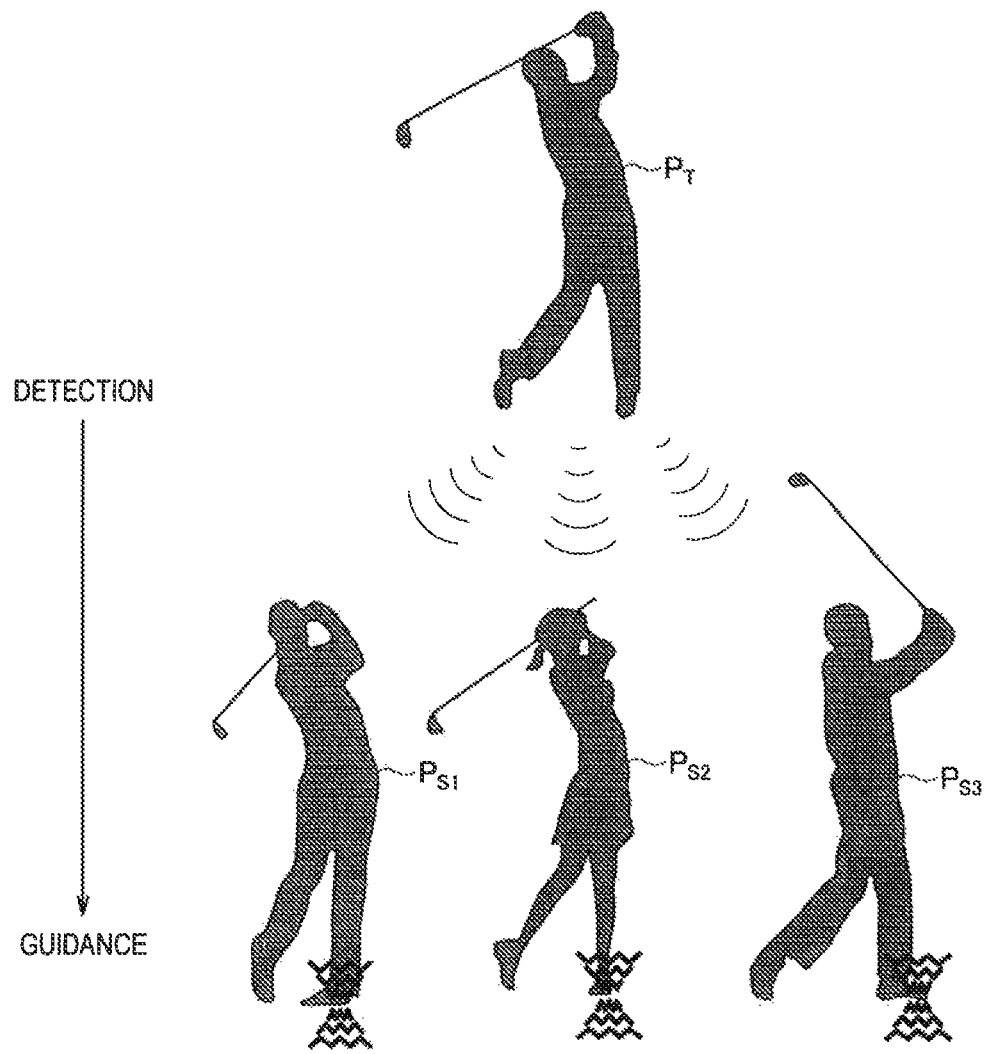

[Fig. 10]
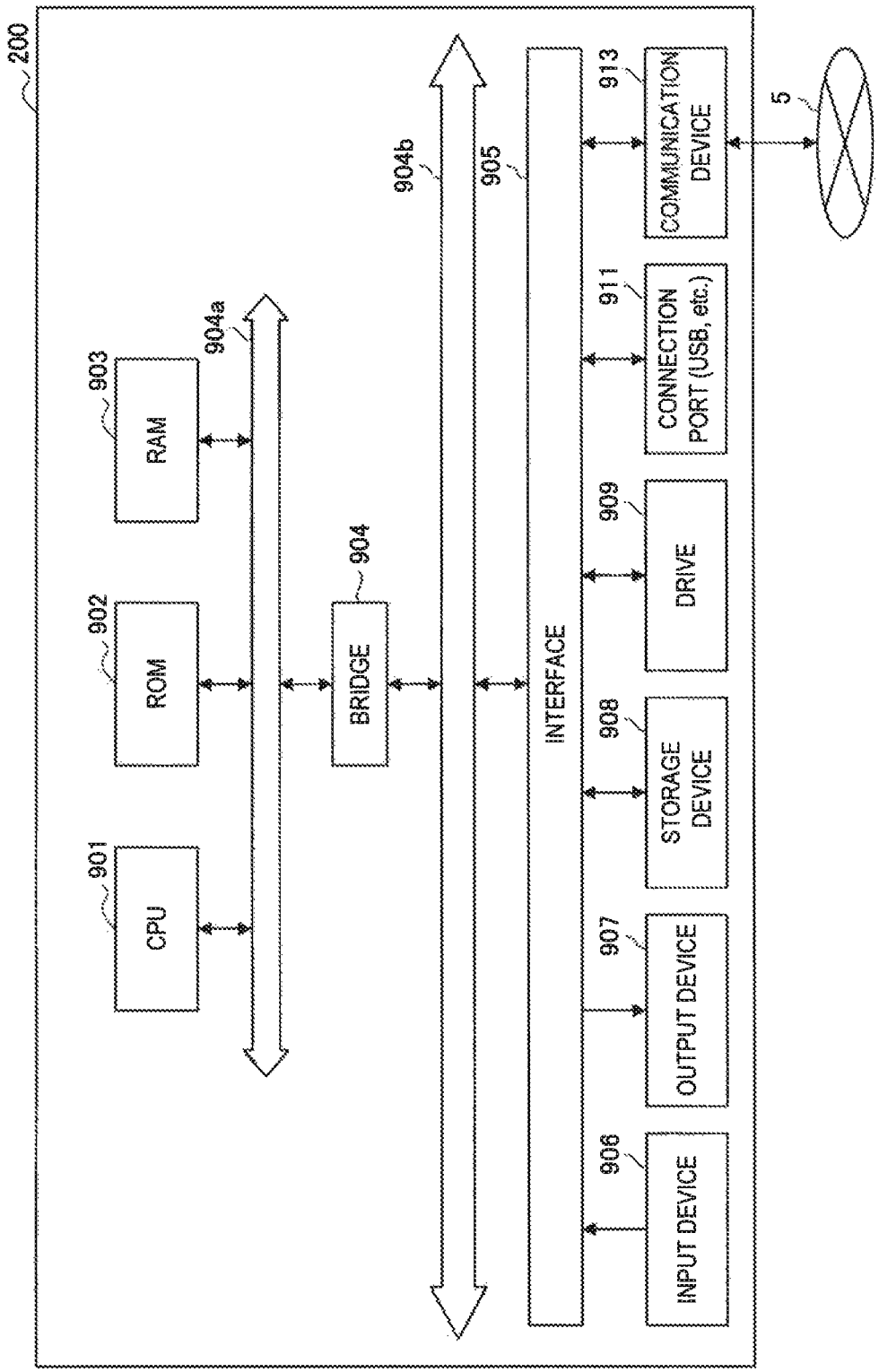

INFORMATION PROCESSING APPARATUS, INFORMATION PROCESSING SYSTEM, AND INSOLE

CROSS REFERENCE TO RELATED APPLICATIONS

This application is a National Stage Patent Application of PCT International Patent Application No. PCT/JP2016/002334 filed May 12, 2016 under 35 U.S.C. § 371, which claims the benefit of Japanese Priority Patent Application JP 2015-118931 filed Jun. 12, 2015, the entire contents of which are incorporated herein by reference.

TECHNICAL FIELD

The present disclosure relates to information processing apparatuses, information processing systems, and insoles.

BACKGROUND ART

In the related art, a technology for detecting weight on soles has been proposed. For example, PTL 1 discloses a foot force sensor including at least two pockets which may be inflated with air or filled with liquid to measure the air or liquid pressure within each pocket using a pressure sensor. The foot force sensor may be formed as an insole worn inside a shoe, for example. The foot force sensor is capable of detecting weight on a sole of a user wearing the shoe with the insole.

CITATION LIST

Patent Literature

[PTL 1]
JP 2005-532138T

SUMMARY

Technical Problem

Unfortunately, according to the related art, it is merely possible to measure distribution of pressure on the sole and display a result of the measurement. Therefore, it is necessary for a user to think and act for oneself in response to the result of measurement.

Accordingly, the present disclosure proposes a novel and improved information processing apparatus, information processing system, and insole capable of using a result of detection of weight on soles and instructing a user how to carry out action.

Solution to Problem

According to an embodiment of the present disclosure, there is provided an information processing apparatus including circuitry configured to acquire weight distribution information of a subject by at least one sensor, analyze the acquired weight distribution information, and initiate a providing of feedback information based on the analyzed weight distribution information.

Further, according to an embodiment of the present disclosure, there is provided an information processing method including acquiring weight distribution information of a subject by at least one sensor, analyzing the acquired weight distribution information, and providing feedback information based on the analyzed weight distribution information.

Further, according to an embodiment of the present disclosure, there is provided a non-transitory computer-readable storage medium having embodied thereon a program, which when executed by a computer causes the computer to execute a method, the method including acquiring weight distribution information of a subject by at least one sensor, analyzing the acquired weight distribution information, and providing feedback information based on the analyzed weight distribution information.

Advantageous Effects of Invention

As described above, according to an embodiment of the present disclosure, it is possible to use a result of detection of weight on soles and instruct a user how to carry out action. Note that the effects described above are not necessarily limited, and along with or instead of the effects, any effect that is desired to be introduced in the present specification or other effects that can be expected from the present specification may be exhibited.

BRIEF DESCRIPTION OF DRAWINGS

FIG. 1 is a diagram illustrating an overview of an information processing system according to an embodiment of the present disclosure.

FIG. 2 is a diagram illustrating a configuration of an insole according to an embodiment.

FIG. 3 is a functional block diagram illustrating a functional configuration of the information processing system according to an embodiment.

FIG. 4 is a flowchart illustrating a process for guiding a user to move his/her weight, the process being carried out by the information processing system according to an embodiment.

FIG. 5 is an explanatory diagram illustrating an example of acquired weight distribution information of a user.

FIG. 6 is an explanatory diagram illustrating comparison between model weight distribution information and weight distribution information of a user.

FIG. 7 is an explanatory diagram illustrating an example of notification of instruction information for guiding a user to move his/her weight.

FIG. 8 is an explanatory diagram illustrating another example of notification of instruction information for guiding a user to move his/her weight.

FIG. 9 is an explanatory diagram illustrating an example of notification of instruction information for guiding a plurality of users to move their weight.

FIG. 10 is a hardware configuration diagram illustrating a hardware configuration of a communication terminal according to an embodiment.

DESCRIPTION OF EMBODIMENTS

Hereinafter, embodiments of the present disclosure will be described in detail with reference to the appended drawings. In this specification and the appended drawings, structural elements that have substantially the same function and structure are denoted with the same reference numerals, and repeated explanation of these structural elements is omitted.

Note that the description is given in the following order.
1. Overview
2. Insole
3. Functional Configuration 4. Processing Flow
5. Use Case
5.1. Skiing and Snowboarding
5.2. Golf and Tennis
5.3. Running
5.4. Other Case
6. Hardware Configuration <1. Overview>

First, with reference to FIG. 1, an overview of a configuration of an information processing system according to an embodiment of the present disclosure is described. FIG. 1 is a diagram illustrating an overview of an information processing system according to an embodiment.

In the information processing system according to an embodiment, weight on soles of a user is detected to instruct the user how to carry out action on the basis of a result of the detection. The weight on the soles of the user is measured by a weight detection apparatus including a pressure sensor. In an embodiment, the weight detection apparatus may be formed as insoles. According to this configuration, the weight on the soles of the user can be detected when the user wears footwear to which the insoles are inserted such as shoes. For example, as illustrated in FIG. 1, weight on soles is detected during skiing when insoles 100R and 100L serving as the weight detection apparatus are inserted into ski boots.

In the information processing system according to an embodiment, detected weight on soles is used for instructing the user how to carry out action. As illustrated in FIG. 1, when a result of detection carried out by the pressure sensor is transmitted to a communication terminal 200 such as a smartphone via wireless communication, the communication terminal 200 analyzes the received weight data and generates weight distribution information that indicates distribution of weight on soles of a user, for example. The weight distribution information includes strength and distribution of weight on the entire soles.

By using the weight distribution information, it is possible to visualize current weight distribution and show the current weight distribution to a user, for example. By displaying weight distribution on a display unit of the communication terminal 200 or an eyewear terminal, it is possible to clearly show a current weight state to a user, for example. According to this configuration, the user can visually recognize the way to put his/her weight on the soles which the user understands only on the basis of his/her feeling without using this configuration. In addition, by comparing distribution of weight of a user with model weight distribution and displaying a result of the comparison, the user can carry out action to remedy his/her own defect. Model weight distribution information is stored in a server 300 as reference information, for example. The model weight distribution information can be acquired by the communication terminal 200 connected to the server 300 via a network.

On the basis of the acquired weight distribution information, the information processing system according to an embodiment can notify instruction information to a user for guiding the user to move his/her weight. For example, a position to be weighted, weight timing, weight strength, and the like to ski well is notified to a user who is skiing. Accordingly, the user can receive specific instructions. For example, it is possible to notify the instruction information to the user by stimulus to soles, audio, display, or the like.

In addition, it is possible to specify a habit, defect, and the like in action of each user by accumulating and analyzing the acquired weight distribution information in the server 300 or the like, for example. By using such analysis data, it is possible to give appropriate advice to each user. For example, by analyzing weight distribution information acquired when a user is skiing to obtain a habit of the user, it is possible to appropriately notify tricks for skiing in a certain course to the user. It is also possible to use habits of users to recommend equipment suitable for each user or possible for an equipment manufacturer to use the habits of users to develop equipment, the habits being obtained by analyzing weight distribution information of the users.

Hereinafter, details of the configuration of the information processing system according to an embodiment are described.

<2. Insole>

First, with reference to FIG. 2, a configuration of an insole is described. The insole functions as the weight detection apparatus for detecting weight on a sole of a user in the information processing system according to an embodiment. FIG. 2 is a diagram illustrating a configuration of an insole 100 according to an embodiment. FIG. 2 illustrates the insole 100 for one foot. Footwear to which the insole 100 is inserted is not limited. The footwear may be sports shoes, ski boots, snowboard boots, golf shoes, tennis shoes, casual shoes, or the like.

The insole 100 according to an embodiment can detect weight on a sole of a user. As illustrated in FIG. 2, pressure sensors 110 and a control unit 120 are provided between an insole bottom 101 and an insole cover 103. In addition, the insole 100 according to an embodiment further includes a sole stimulation mechanism 130 as a stimulus generation unit for notifying instruction information to the user. In the example in FIG. 2, the pressure sensors 110 also functions as the sole stimulation mechanisms 130.

For example, the insole bottom 101 and insole cover 103 may be formed from materials similar to a common insole. Quality and thickness of the materials may be appropriately set in view of a detection property and the like of the pressure sensors 110. As illustrated in FIG. 2, in the insole 100 according to an embodiment, a sensor unit (pressure sensors 110, control unit 120, and sole stimulation mechanisms 130) is sandwiched between the insole bottom 101 and the insole cover 103. According to this configuration, it is possible to commonalize the sensor unit and easily follow change in size of footwear. In other words, the size of the insole 100 can be easily changed by changing the size of the insole bottom 101 and the insole cover 103 that sandwich the sensor unit.

The pressure sensor 110 is a sensor for measuring distribution of pressure on a sole. As the pressure sensor 110, a film-laminated-type pressure sensor for measuring electrical resistance values, a sensor using a piezoelectric element, or the like may be used, for example. As illustrated in FIG. 2, a plurality of the pressure sensors 110 may be provided to acquire weight on the entire sole, or a sensor capable of acquiring weight on the entire sole by using one device may be used. The pressure sensor 110 output a result of detection to the control unit 120.

The control unit 120 controls the pressure sensors 110 and the sole stimulation mechanisms 130. When the control unit 120 receives the result of detection from the pressure sensors 110, the control unit 120 outputs the result to the communication terminal 200 as detection data, or records the result in memory in the control unit 120, for example. The control unit 120 controls the sole stimulation mechanisms 130 on the basis of instruction information when receiving the instruction information from the communication terminal 200.

The sole stimulation mechanism 130 is a mechanism for notifying information to a user by stimulating a sole of the user. As the sole stimulation mechanism 130, a mechanism for generating vibration stimulus, deformation stimulus, electrical stimulus, or the like may be used. The vibration stimulus may be generated using a vibrator, a piezoelectric element, or the like. The deformation stimulus may be generated by changing the thickness of an insole using a piezoelectric element or the like. The electrical stimulus may be generated by electrifying a human body using low-frequency and mild electricity, for example. In the case where the piezoelectric element is used, the pressure sensor 110 also functions as the sole stimulation mechanism 130, for example. The control unit 120 controls drive of the sole stimulation mechanism 130.

<3. Functional Configuration>

Next, with reference to FIG. 3, a functional configuration of the information processing system according to an embodiment is described. FIG. 3 is a functional block diagram illustrating the functional configuration of the information processing system according to an embodiment. As illustrated in FIG. 3, the information processing system according to an embodiment includes the insole 100, the communication terminal 200, and the server 300. According to the configuration of the information processing system according to an embodiment, the communication terminal 200 may be able to acquire detection information also from a video camera 400 or various kinds of sensors 500, for example.

(Insole)

The insole 100 can detect weight on a sole of a user. As illustrated in FIG. 3, the insole 100 includes the pressure sensor 110, the control unit 120, and the sole stimulation mechanism 130. The specific configuration example of the insole 100 is illustrated in FIG. 2 as described above. As illustrated in FIG. 3, the control unit 120 includes a communication unit 121 for exchanging information with external equipment such as the communication terminal 200, an information processing unit 123 for processing various kinds of information, and a battery 125 serving as power source for driving the pressure sensor 110, the control unit 120, and the sole stimulation mechanism 130. In addition, the control unit 120 may include memory (not illustrated) for storing a result of detection carried out by the pressure sensor 110.

Weight on a sole measured by the pressure sensor 110 is output to the control unit 120. The information processing unit 123 in the control unit 120 stores the result of detection carried out by the pressure sensor 110 as weight data, and transmits the weight data to the communication terminal 200 via the communication unit 121, Communication between the communication unit 121 and a communication unit 210 of the communication terminal 200 can be established using a wireless communication function such as Bluetooth (registered trademark).

The insole is also capable of receiving instruction information to a user from the communication terminal 200 via the communication unit 121. The information processing unit 123 drives the sole stimulation mechanism 130 on the basis of the instruction information. According to this configuration, it is possible to notify the instruction information to the user by stimulating a sole of the user.

The control unit 120 in the insole 100 may include a USB terminal (not illustrated). Since the USB terminal is provided, it is possible to charge the battery 125 with electricity from outside, and it is possible to take various kinds of setting of the control unit 120 and data stored in the memory, for example. The USB terminal may be mounted under an arch of a foot in order to reduce feeling of strangeness of a user wearing footwear to which the insole is inserted.

FIG. 3 illustrates the configuration of the insole 100 of one foot. In the case of acquiring weight distribution information of both feet, an insole of another foot is formed in a similar way.

(Communication Terminal)

The communication terminal 200 is equipment such as a smartphone, a tablet terminal, or a wearable device including an eyewear terminal and the like, for example. As illustrated in FIG. 3, the communication terminal 200 includes the communication unit 210, a weight-distribution-information generation unit 220, an instruction-information generation unit 230, a display unit 240, and an audio output unit 250.

The communication unit 210 is a function unit for exchanging information with the insole 100, the server 300, the video camera 400, the various kinds of sensors 500, and the like. The communication unit 210 has one or a plurality of communication functions each of which corresponds to a communication mode of each equipment. For example, the communication unit 210 communicates with the insole 100 using Bluetooth (registered trademark), and exchanges information with the server 300 via a network.

The weight-distribution-information generation unit 220 processes weight data on a sole of a user input from the insole 100, and generates weight distribution information. The weight distribution information includes a position and strength of weight on the sole. The weight-distribution-information generation unit 220 may output the generated weight distribution information to the display unit 240 and notify the information to the user through display. At this time, as illustrated in FIG. 1, the weight distribution information may be illustrated in an isobar image, for example. According to this configuration, it is possible to show visually understandable information to a user. In addition, the weight-distribution-information generation unit 220 outputs the generated weight distribution information to instruction-information generation unit 230.

The instruction-information generation unit 230 generates instruction information to the user on the basis of the acquired weight distribution information of the user. For example, the instruction-information generation unit 230 compares model weight distribution information with the weight distribution information of the user, and generates information for guiding the user to carry out action ideally as the instruction information. Specifically, the instruction-information generation unit 230 generates instruction information for stimulating a sole of the user and prompting the user to change a way to put his/her weight on the sole in a manner that the weight distribution information of the user approaches the model weight distribution information. In this case, it is also possible for the instruction-information generation unit 230 to learn the change or the like in the weight distribution information of the user after receiving past instruction information, and acquire a way to guide a position to be weighted, strength of stimulus, and the like to approach the ideal weight distribution.

The instruction-information generation unit 230 may constantly generate instruction information and constantly notify instruction information to the user. Alternatively, the instruction-information generation unit 230 may generate instruction information and notify instruction information to the user in the case where difference from the model weight distribution information exceeds a predetermined value. In this case, no instruction is issued when action of the user is correct. Therefore, the user can learn a correct way to put his/her weight on the soles while checking whether his/her action is correct.

The instruction-information generation unit 230 notifies the instruction information to the user after generating the instruction information. Therefore, for example, the instruction information is transmitted to the insole 100 via the communication unit 210. The insole 100 stimulates a sole of the user and notifies a way to put his/her weight on the sole to the user by driving the sole stimulation mechanism 130 on the basis of the received instruction information. Alternatively, the instruction-information information unit 230 may also notify a way to put his/her weight on the sole to the user by displaying a position to be weighted on the display unit 240 or by outputting audio from the audio output unit 250.

(Server)

The server 300 includes a database 310 in which model weight distribution information is stored. In response to a request from the communication terminal 200, the server 300 outputs the model weight distribution information to the communication terminal 200. The server 300 may store weight data of each user acquired from the insole 100. In this case, the weight data is stored in association with time of detection. In the case where the server 300 is capable of acquiring another sensor information acquired at the time when weight data is acquired, the server 300 may store the weight data in association with such information. The another sensor information includes an image captured by the video camera 400, position information acquired by a GPS or the like, and a value detected by a gyro sensor included in a wearable device worn by the user, for example. By associating the weight information with such sensor information, it is possible to recognize a site and details of action during the weight data is being acquired. It is also possible to give more understandable instructions to the user by issuing the instruction information in combination with the captured image, for example, in the case where the instruction information is notified to the user.

The configuration example of the information processing system according to an embodiment has been described. Note that, each function unit in the communication terminal 200 and the server 300 illustrated in FIG. 3 does not have to be provided in each apparatus in the way as illustrated in FIG. 3. Each function unit may be provided in any of the communication terminal 200 and the server 300. For example, the weight-distribution-information generation unit 220 and the instruction-information generation unit 230 are provided in the communication terminal 200 in FIG. 3. However, the weight-distribution-information generation unit 220 and the instruction-information generation unit 230 may be provided in the server 300. In addition, with reference to FIG. 3, the display unit 240 and the audio output unit 250 do not have to be provided in the communication terminal 200. The communication terminal 200 may use a display apparatus and a speaker in equipment different from the communication terminal 200.

<4. Processing Flow>

With reference to FIGS. 4 to 8, a process for guiding a user to move his/her weight is described, the process being carried out by the information processing system according to an embodiment. FIG. 4 is a flowchart illustrating a process for guiding a user to move his/her weight, the process being carried out by the information processing system according to an embodiment. FIG. 5 is an explanatory diagram illustrating an example of acquired weight distribution information of a user. FIG. 6 is an explanatory diagram illustrating comparison between model weight distribution information and weight distribution information of a user. FIG. 7 is an explanatory diagram illustrating an example of notification of instruction information for guiding a user to move his/her weight. FIG. 8 is an explanatory diagram illustrating another example of notification of instruction information for guiding a user to move his/her weight.

As illustrated in FIG. 4, in the process for guiding a user to move his/her weight carried out by the information processing system according to an embodiment, weight data is first acquired (S10). The weight data is a result of detection carried out by the pressure sensors 110 of the insoles 100. The control unit 120 of each of the insoles 100 transmits the weight data to the communication terminal 200 via the communication unit 121.

Next, the communication terminal 200 generates weight distribution information by using the weight-distribution-information generation unit 220 (S20). The weight distribution information is information including positions and strength of weight obtained from the weight data acquired at a plurality of positions. The weight distribution information may be acquired at predetermined intervals. According to this configuration, the user can recognize change in the distribution of weight on soles of the user. As illustrated in FIG. 5, the distribution of weight on soles of the user turning left in skiing changes from moment to moment. For example, between time A and time F, a weight state changes from a state where a big-toe side of each foot is weighted to a state where his/her weight is shifted to the left side of each foot, and then to a state where his/her weight is returned to the big-toe side of each foot. By recording and holding such weight distribution information, secondary use of the weight distribution information is also possible as judgment information for analyzing a habit, defect, and the like in action of the user, and for providing the user with appropriate information, for example. Details of the secondary use of the weight distribution information are described later.

When the weight distribution information is acquired, the instruction-information generation unit 230 generates instruction information to the user on the basis of the weight distribution information (S30). The instruction information gives the user instructions on a model way to put his/her weight on the sole with respect to action to be carried out by the user. For example, as illustrated in FIG. 6, although both a teacher acting as a role model and the user put their weight on the left sides, positions to be strongly weighted are different between the teacher and the user with respect to the ways to put their weight on the sole when turning left in skiing. Accordingly, the instruction information is notified to the user to carry out action in a manner that the user's weight distribution approaches a model weight distribution.

The instruction to the user may be given by stimulating the soles of the user, for example. At this time, the instruction information is stimulus information for stimulating the soles of the user. The soles of the user are stimulated by driving the sole stimulation mechanisms 130 provided in the insoles 100. The sole stimulation mechanism 130 may be configured to generate vibration stimulus, deformation stimulus, electrical stimulus, or the like. The instruction-information generation unit 230 compares model weight distribution information with the detected weight distribution information of the user, and generates stimulus information for guiding the distribution of the weight of the user to approach the model weight distribution according to difference in position and strength of weight between the distribution of the weight of the user and the model weight distribution.

In addition to the stimulus information for generating stimulus to the soles of the user, the instruction information may be display instruction information for causing the display unit 240 to display a position to be weighted, audio instruction information for causing the audio output unit 250 to output instructions by audio, or the like, for example.

When the instruction information is generated, instructions are given to the user on the basis of the instruction information (S40). For example, in the case where the instruction information is stimulus information for stimulating the soles of the user, the instruction information generated by the instruction-information generation unit 230 is output to the insoles 100 via the communication unit 210. Each of the insoles 100 receiving the instruction information drives the sole stimulation mechanisms 130 on the basis of the instruction information by using the information processing unit 123. The user is stimulated by the sole stimulation mechanisms 130 and recognizes which position to shift his/her weight to.

In the case where the instruction information is the display instruction information or the audio instruction information, the instruction-information generation unit 230 may output the instruction information to the display unit 240 or the audio output unit of the communication terminal 200, and notify the instruction information to the user, for example. Equipment other than the communication terminal 200 may notifies such information. For example, another equipment worn by the user may notify such information. In addition, the instruction information may be notified to the user by combining stimulus, display, audio, and the like.

The process for guiding a user to move his/her weight has been described, the process being carried out by the information processing system according to an embodiment. According to an embodiment, weight distribution information of soles of a user is generated, the weight distribution information is compared with weight distribution serving as a model of action carried out by the user, instruction information for guiding the user's way to put his/her weight on the soles to approach the model is generated, and the instruction information is notified to the user. According to this configuration, the user can receive clear instructions and easily carry out action to approach correct action.

<5. Use Case>

(5.1. Skiing and Snowboarding)

The information processing system according to an embodiment can be applied to ski and snowboard lessons, for example. In skiing and snowboarding, ways to shift weight are different in each action such as turning and stopping. The user can carry out action better by shifting his/her weight in the right way. However, it is difficult for the user to clearly recognize a position to be weighted from verbal instructions provided by a teacher with respect to a way to shift one's weight. In addition, it is also difficult to understand whether the user shifts his/her weight correctly on the basis of instructions. Therefore, the information processing system according to an embodiment is capable of giving understandable instructions to a user by acquiring weight distribution information of the user, comparing the weight distribution information of the user with model weight distribution, and notifying a correct way to shift his/her weight to the user.

(Acquisition of Weight Distribution and Weight Guidance)

Specifically, first, weight distribution information acquired by detecting weight on the soles of a user is visualized as illustrated in FIG. 1, and the weight distribution information is notified to the user, for example. Thereby, it is possible to cause the user to recognize a current weight state. In this case, it is possible to cause the user to visually recognize difference from correct weight distribution by displaying the weight distribution information of the user together with model weight distribution.

In addition, according to the information processing system, it is possible to generate instruction information using the instruction-information generation unit 230 by comparing the distribution of weight of the user with the model weight distribution, directly instruct the user on a correct way to put his/her weight on the soles, and guide the user to correctly put his/her weight on the soles.

For example, it is possible to guide the user with respect to a position, strength, and timing of weight, by transmitting stimulus information to the insoles 100 in the ski boots worn by the user and stimulating the soles of the user with vibration or the like.

Alternatively, as illustrated in FIG. 7, a display apparatus 10 displays video of model action and model distribution of weight on soles during indoor virtual training, and weight on the soles of a user during the virtual training is detected to compare and display the model distribution of weight on soles and the distribution of weight of the user. In this case, the insoles 100 capable of detecting weight on soles are inserted in footwear worn by the user. According to this configuration, it is possible to display distribution of weight on the soles when the user carries out action according to the video of model action. In addition, indication to prompt the user to shift his/her weight to a position to be weighted may be displayed on an image of the distribution of weight of the user displayed on the display apparatus 10, at a timing to put his/her weight on the soles. Alternatively, in the case where the insoles 100 include the sole stimulation mechanisms 130, the soles of the user may be stimulated at a timing to put his/her weight on the soles so as to guide the user to carry out action similar to a model position to be weighted and model weight distribution.

In addition, as illustrated in FIG. 8, it is also possible to stimulate the soles of a student $P_S$ who is skiing behind a teacher $P_T$ to tell the student $P_S$ distribution of weight on the soles of the teacher $P_T$ skiing in front of the student $P_S$, so as to teach a way to shift his/her weight. In this case, insoles 100 capable of detecting weight on soles and stimulating the soles are inserted in ski boots worn by the teacher $P_T$ and the student $P_S$. In addition, position information of the teacher $P_T$ and the student $P_S$ may be acquired. The communication terminal 200 acquires distribution of weight on the soles of the teacher $P_T$, and detects a position in which the way to put his/her weight on the soles of the teacher $P_T$ is changed. Subsequently, the communication terminal 200 generates instruction information indicating how the teacher $P_T$ has put his/her weight on the soles before the student $P_S$ skiing behind the teacher $P_T$ passes through the position, and the communication terminal 200 drives the sole stimulation mechanisms 130 in the insoles 100 of the student $P_S$. According to this configuration, the student PS can clearly recognize a way to put his/her weight on the soles.

In the case the teacher $P_T$ teaches only one student $P_S$, the sole stimulation mechanisms 130 of the insoles of the student $P_S$ may be driven at the same timing when the distribution of weight on the soles of the teacher $P_T$ is acquired. In this case, the student $P_S$ can feel change in weight on the soles of the teacher $P_T$ while watching the action carried out by the teacher $P_T$. Thereby, the student $P_S$ can recognize a way to put his/her weight on the soles more clearly.

(Secondary Use of Data)

In the information processing system according to an embodiment, detected weight distribution information of a user may be accumulated. By using the accumulated weight distribution information, it is possible to analyze and recognize a habit, defect, and the like in action of each user, for example. In addition, it is also possible to recognize a degree of proficiency as the user keeps practicing. Alternatively, by providing companies with the accumulated weight distribution information, it is also possible to use habits and the like of users to recommend equipment suitable for each user or possible to use the habits and the like of users to develop equipment, the equipment corresponding to the habits and the like of each user. In addition, record of the action and the weight distribution information of the teacher may be sold as teaching materials for users by recoding the action and the weight distribution information of the teacher. Moreover, more useful accumulated weight distribution information is obtained by recoding other information in addition to the weight distribution information, such as video, GPS information, and the like that are acquired at the same time when the weight distribution information is acquired.

(5.2. Golf and Tennis)

The information processing apparatus according to an embodiment can be applied to golf and tennis lessons, for example. Acquisition of weight distribution information of a user enables analysis of habits and defect of the user, analysis of variation in condition, and acquisition of traps in each course or court. In addition, more detailed analysis can be carried out by aligning weight distribution information of each shot and information on course, court, score, and the like.

Swing information and weight distribution information of the soles may be analyzed together in cooperation with a swing sensor. For example, in the case of golf, club head speed, a trajectory of a club or hands during downswing and backswing, time, and the like are acquired as the swing information. According to this configuration, ideal weight guidance can be carried out in tandem with the swing. At this time, video in which the swing carried out by the user is captured may be additionally analyzed.

On the other hand, weight distribution information, swing information, and video of a teacher may be acquired and used as teaching materials for a user. When the user practice while the display apparatus displays video of the swing carried out by the teacher and weight distribution at this time, distribution of weight on the soles of the user may be acquired and displayed on the display apparatus. According to this configuration, the user can practice while recognizing difference from the model. In addition, a way to put his/her weight on the soles may be instructed by driving the sole stimulation mechanisms in the insoles of the user at a timing when the club is to be swung.

Alternatively, a way to put weight on the soles of the teacher may be notified to the student by acquiring weight distribution information of the soles of the teacher at the time when the teacher actually swings the club. At this time, as illustrated in FIG. 9 for example, weight distribution information of one teacher $P_T$ may be notified to a plurality of students $P_{S1}$ to $P_{S3}$ at the same time. According to this configuration, the plurality of students $P_{S1}$ to $P_{S3}$ can clearly recognize how the teacher has shifted his/her weight at the time when the teacher has swung his/her club. At this time, the teacher $P_T$ and the students $P_{S1}$ to $P_{S3}$ do not have to be in the vicinity of each other. It is only necessary for insoles and communication terminals of the teacher $P_T$ and the students $P_{S1}$ to $P_{S3}$ to be able to communicate with each other. For example, in the case where the communication terminals 200 are smartphones, the teacher can teach the students even in a remote location by using communication functions of the smartphones.

Also in the present example, it is possible to analyze and recognize a habit, defect, and the like in action of each user by accumulating weight distribution information of each user detected as described above. In addition, it is possible to recognize more detailed features of action by recoding traps for each user in each course. Since such information is accumulated, it is also possible to recognize a degree of proficiency as the user keeps practicing. Alternatively, by providing companies with the accumulated weight distribution information, it is also possible to use habits and the like of users to recommend equipment suitable for each user or possible to use the habits and the like of users to develop equipment, the equipment corresponding to the habits and the like of each user. In addition, record of the action and the weight distribution information of the teacher may be sold as teaching materials for users by recoding the action and the weight distribution information of the teacher.

(5.3. Running)

The information processing system according to an embodiment can be applied to a running lesson, for example. Acquisition of weight distribution information of a user enables analysis of a running form of a user. In addition, acquisition of various kinds of sensor information such as GPS, time, heartbeat enables analysis of more detailed characteristics of the user, measurement of an amount of exercise (calorie counting), and the like.

In addition, by providing the user with instruction information, it is possible to set a pace of running and to improve a running form (to teach the way to put his/her weight on the sole and how to kick). In addition, the user can be guided with respect to a running course by using the instruction information. The course guidance using the instruction information enables the user to run without using map or audio guidance and without any stress.

Also in the present example, it is possible to analyze and recognize a habit, defect, and the like in action of each user by accumulating weight distribution information of each user detected as described above. In addition, it is possible to recognize more detailed features of action by recoding traps for each user in each course. Since such information is accumulated, it is also possible to recognize a degree of proficiency as the user keeps practicing. Alternatively, by providing companies with the accumulated weight distribution information, it is also possible to use habits and the like of users to recommend equipment suitable for each user or possible to use the habits and the like of users to develop equipment, the equipment corresponding to the habits and the like of each user. In addition, record of the action and the weight distribution information of the teacher may be sold as teaching materials for users by recoding the action and the weight distribution information of the teacher.

(5.4. Other Case)

In addition to the above described examples, the information processing system according to an embodiment can be used for healthcare application such as check, correction, and the like of posture and a way someone walks. In addition, it is also possible to teach steps in dancing, measure an amount of exercise in walking, indicate a direction, for example. In addition, by inserting the insoles according to an embodiment in footwear worn by a child, it is possible to stimulate the soles of the child in order to monitor action carried out by the child or just for enjoyment.

Alternatively, in the case where the information processing system according to an embodiment is used when someone rides a bicycle, it is possible to acquire information such as timing, intensity, and the like of power to pedal in addition to mere measurement of rotation speed of pedal (cadence). According to this configuration, detection together with GPS information enables measurement of an amount of exercise and determination of whether a selected gear is appropriate during running.

<6. Hardware Configuration>

A hardware configuration example of the communication terminal 200 of the information processing system according to an embodiment is described. FIG. 10 is a hardware configuration diagram illustrating a hardware configuration of the communication terminal 200 according to the above embodiments.

As described above, the communication terminal 200 according to an embodiment can be achieved by a processing apparatus such as a computer. As illustrated in FIG. 10, the communication terminal 200 includes a central processing unit (CPU) 901, read only memory (ROM) 902, random access memory (RAM) 903, and a host bus 904a. In addition, the communication terminal 200 includes a bridge 904, an external bus 904b, an interface 905, an input device 906, an output device 907, a storage device 908, a drive 909, a connection port 911, and a communication device 913.

The CPU 901 functions as an arithmetic device and a control device to control all of the operating processes in the communication terminal 200 in accordance with various kinds of programs. The CPU 901 may be a microprocessor. The ROM 902 stores programs, operation parameters, and the like used by the CPU 901. The RAM 903 transiently stores programs used when the CPU 901 is executed, and parameters that change as appropriate when executing such programs. The CPU 901, the ROM 902, and the RAM 903 are connected to each other via the host bus 904a configured of a CPU bus or the like.

The host bus 904a is connected to the external bus 904b such as a Peripheral Component Interconnect/Interface (PCI) bus via the bridge 904. The host bus 904a, the bridge 904 and the external bus 904b are not necessarily separated from one another, and their functions may be implemented by one bus.

The input device 906 includes: an input mechanism used by the user for imputing information, such as a mouse, a keyboard, a touch screen, a button, a microphone, a switch, or a lever; an input control circuit configured to generate an input signal based on user input and to output the signal to the CPU 901; and the like. The output device 907 includes an audio output apparatus such as a speaker and a display device such as a liquid crystal display (LCD) device, an organic light emitting diode (OLED) device, or a lamp, for example.

The storage device 908 is a device for data storage which is configured as an example of a storage unit of the communication terminal 200. The storage device 908 may include a storage medium, a recording device which records data in a storage medium, a reader device which reads data from a storage medium, a deletion device which deletes data recorded in a storage medium, and the like. The storage device 908 drives solid-state memory and stores therein the programs executed by the CPU 901 and various data.

The drive 909 is a reader/writer for a storage medium, and is incorporated in or externally attached to the communication terminal 200. The drive 909 reads information recorded on a removable recording medium that is mounted such as semiconductor memory, and outputs the information to the RAM 903.

The communication port 911 is an interface for connection to external equipment, and is, for example, a connection port for connection to external equipment that can transmit data via a Universal Serial Bus (USB). The communication device 913 is, for example, a communication interface including a communication device for connection to a communication network 5. The communication device 913 may be a communication device corresponding to Bluetooth (registered trademark), a communication device corresponding to a wireless local area network (LAN), a communication device corresponding to a wireless USB, or a wire communication device that performs wired communication.

It should be understood by those skilled in the art that various modifications, combinations, sub-combinations and alterations may occur depending on design requirements and other factors insofar as they are within the scope of the appended claims or the equivalents thereof.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1) An information processing apparatus including:
circuitry configured to:
acquire weight distribution information of a subject by at least one sensor;
analyze the acquired weight distribution information; and
initiate a providing of feedback information based on the analyzed weight distribution information.

(2) The information processing apparatus according to (1), wherein the subject is a person.

(3) The information processing apparatus according to (2), wherein the subject is an object.

(4) The information processing apparatus according to any of (1) to (3), wherein the feedback information provides guidance for moving or shifting weight of the subject.

(5) The information processing apparatus according to any of (1) to (4), wherein the feedback information comprises instruction data.

(6) The information processing apparatus according to any of (1) to (5), wherein the feedback information comprises weight distribution data including strength and distribution of weight.

(7) The information processing apparatus according to any of (1) to (6), wherein the feedback information is provided via a display.

(8) The information processing apparatus according to any of (1) to (7), wherein the feedback information is provided via an eyewear terminal.

(9) The information processing apparatus according to any of (1) to (8), wherein the feedback information is provided via a touch panel.

(10) The information processing apparatus according to any of (1) to (9), wherein the feedback information is provided via a speaker.

(11) The information processing apparatus according to any of (1) to (10), wherein the feedback information is provided by stimulus to a sole.

(12) The information processing apparatus according to any of (1) to (11), wherein the acquired weight distribution information is analyzed by comparing the acquired weight distribution information to a model weight distribution information.

(13) The information processing apparatus according to any of (1) to (12), wherein the feedback information is generated based on a result of the comparison of the acquired weight distribution information to the model weight distribution information.

(14) The information processing apparatus according to any of (1) to (13), wherein the feedback information is provided when a difference between the acquired weight distribution information and the model weight distribution information exceeds a predetermined value.

(15) The information processing apparatus according to any of (1) to (14), wherein the acquired weight distribution information is analyzed by comparing the acquired weight distribution information to weight distribution information of another subject.

(16) The information processing apparatus according to any of (1) to (15), wherein the feedback information is generated based on a result of the comparison of the acquired weight distribution information to the weight distribution information of another subject.

(17) The information processing apparatus according to any of (1) to (16), wherein the feedback information is provided when a difference between the acquired weight distribution information and the weight distribution information of another subject exceeds a predetermined value.

(18) The information processing apparatus according to any of (1) to (17), wherein the acquired weight distribution information is stored with associated time of detection.

(19) The information processing apparatus according to any of (1) to (18), wherein the weight distribution information is determined based on a detected weight on a sole of the subject.

(20) An information processing method, the method being executed by a processor having circuitry, and including:
acquiring weight distribution information of a subject by at least one sensor;
analyzing the acquired weight distribution information; and
providing feedback information based on the analyzed weight distribution information.

(21) A non-transitory computer-readable storage medium storing a program which, when executed by a computer having circuitry, causes the computer to execute a method, the method including:
acquiring weight distribution information of a subject by at least one sensor;
analyzing the acquired weight distribution information; and
providing feedback information based on the analyzed weight distribution information,

(22) An information processing apparatus including:
a weight-distribution-information generation unit configured to acquire weight distribution information of a sole of a user on the basis of weight detection information detected by a pressure sensor provided on the sole; and
an instruction-information generation unit configured to generate instruction information to be notified to the user on the basis of the weight distribution information.

(23) The information processing apparatus according to (22), wherein the instruction information is stimulus information for stimulating the sole of the user.

(24) The information processing apparatus according to (23), wherein the stimulus information is information for generating at least one of vibration stimulus, deformation stimulus, and electrical stimulus.

(25) The information processing apparatus according to (23) or (24), wherein the instruction-information generation unit changes strength of stimulus to the sole according to weight intensity included in the weight detection information.

(26) The information processing apparatus according to any one of (22) to (25), wherein the instruction information is weight guidance information that indicates a position to be weighted to the user.

(27) The information processing apparatus according to (26), wherein the weight guidance information is presented through at least one of video and audio.

(28) The information processing apparatus according to any one of (22) to (27), wherein the instruction-information generation unit generates the instruction information by comparing the weight distribution information of the user with reference information that indicates weight intensity distribution of sample action.

(29) The information processing apparatus according to any one of (22) to (28), wherein the instruction-information generation unit generates instruction information for driving equipment that notifies an instruction to the user in tandem with weight detection information of the user or a third person.

(30) The information processing apparatus according to any one of (22) to (29), wherein the instruction-information generation unit generates instruction information for driving equipment that notifies an instruction to the user in tandem with sensor information detected by a sensing device worn by the user or a third person.

(31) The information processing apparatus according to any one of (22) to (30), wherein the instruction-information generation unit generates instruction information for driving equipment that notifies an instruction to the user in tandem with video in which the user or a third person is captured.

(32) The information processing apparatus according to any one of (22) to (31), including a communication unit capable of communicating with an insole communication unit provided on an insole of the user.

(33) The information processing apparatus according to any one of (22) to (32), wherein the instruction-information generation unit generates instruction information for one or a plurality of pieces of control target equipment.

(34) The information processing apparatus according to any one of (22) to (33), wherein the instruction-information generation unit generates information that indicates a direction where the user goes.

(35) The information processing apparatus according to any one of (22) to (34), including a storage unit configured to accumulate the weight distribution information acquired by the weight-distribution-information generation unit.

(36) The information processing apparatus according to (35), including an analysis unit configured to analyze an action characteristic of the user on the basis of the accumulated weight distribution information.

(37) An information processing system including:
a pressure detection unit configured to acquire weight detection information of a sole of a user;
a weight-distribution-information generation unit configured to acquire weight distribution information of the sole on the basis of the detected weight detection information; and
an instruction-information generation unit configured to generate instruction information to be notified to the user on the basis of the weight distribution information.

(38) An insole including:
a communication unit configured to exchange information with an external apparatus;
a pressure detection unit configured to acquire weight distribution information of a sole; and
a stimulus generation unit configured to stimulate a specific part of the sole on the basis of instruction information generated on the basis of the weight distribution information.

REFERENCE SIGNS LIST 100 insole
101 insole bottom
103 insole cover
110 pressure sensor
120 control unit
121 communication unit
123 information processing unit
125 battery
130 sole stimulation mechanism
200 communication terminal
210 communication unit
220 weight-distribution-information generation unit
230 instruction-information generation unit
240 display unit
250 audio output unit
300 server
310 database
400 video camera
500 various kinds of sensors

The invention claimed is:

1. An information processing apparatus comprising:
a communication device; and
circuitry configured to:
  acquire weight distribution information of a subject measured by at least one sensor;
  acquire another weight distribution information of another subject measured by another at least one sensor;
  analyze the acquired weight distribution information by comparing the acquired weight distribution information to the acquired another weight distribution information;
  generate feedback information based on the analyzed weight distribution information; and
  initiate an outputting, by the communication device, of the feedback information to an output device to output the feedback information to the subject,
wherein the communication device is configured to output the feedback information to the output device so as to enable the output device to output the feedback information to the subject.

2. The information processing apparatus according to claim 1, wherein the subject is a person.

3. The information processing apparatus according to claim 1, wherein the subject is an object.

4. The information processing apparatus according to claim 1, wherein the feedback information provides guidance for moving or shifting weight of the subject.

5. The information processing apparatus according to claim 1, wherein the feedback information comprises instruction data.

6. The information processing apparatus according to claim 1, wherein the feedback information comprises weight distribution data including strength and distribution of weight.

7. The information processing apparatus according to claim 1, wherein the output device includes a display.

8. The information processing apparatus according to claim 1, wherein the output device includes an eyewear terminal.

9. The information processing apparatus according to claim 1, wherein the output device includes a touch panel.

10. The information processing apparatus according to claim 1, wherein the output device includes a speaker.

11. The information processing apparatus according to claim 1, wherein the output device includes a stimulation mechanism, and
wherein the stimulation mechanism generates stimulus to a sole.

12. The information processing apparatus according to claim 1, wherein the acquired weight distribution information is analyzed by comparing the acquired weight distribution information to a model weight distribution information.

13. The information processing apparatus according to claim 12, wherein the feedback information is generated based on a result of the comparison of the acquired weight distribution information to the model weight distribution information.

14. The information processing apparatus according to claim 12, wherein the feedback information is outputted when a difference between the acquired weight distribution information and the model weight distribution information exceeds a predetermined value.

15. The information processing apparatus according to claim 1, wherein the feedback information is generated based on a result of the comparison of the acquired weight distribution information to the acquired another weight distribution information.

16. The information processing apparatus according to claim 1, wherein the feedback information is outputted when a difference between the acquired weight distribution information and the acquired another weight distribution information exceeds a predetermined value.

17. The information processing apparatus according to claim 1, wherein the acquired weight distribution information is stored with associated time of detection.

18. The information processing apparatus according to claim 1, wherein the weight distribution information is determined based on a detected weight on a sole of the subject.

19. The information processing apparatus according to claim 1, wherein the circuitry is further configured to:
acquire position information of the subject and the another subject; and
control the outputting of the feedback information to the subject at a timing based on the acquired position information of the subject and the another subject.

20. The information processing apparatus according to claim 19, wherein the circuitry is further configured to:
control the outputting of the feedback information to the subject at the timing based on a currently acquired position information of the subject and a previously acquired position information of the another subject.

21. An information processing method, the method being executed via a processor having circuitry, and comprising:
acquiring weight distribution information of a subject measured by at least one sensor;
acquiring another weight distribution information of another subject measured by another at least one sensor;

analyzing the acquired weight distribution information by comparing the acquired weight distribution information to the acquired another weight distribution information;

generating feedback information based on the analyzed weight distribution information; and outputting, by a communication device, feedback information to an output device to output the feedback information to the subject, wherein the feedback information is output by the communication device to the output device so as to enable the output device to output the feedback information to the subject.

22. A non-transitory computer-readable storage medium storing a program which, when executed by a computer having circuitry, causes the computer to execute a method, the method comprising:

acquiring weight distribution information of a subject measured by at least one sensor;

acquiring another weight distribution information of another subject measured by another at least one sensor;

analyzing the acquired weight distribution information by comparing the acquired weight distribution information to the acquired another weight distribution information;

generating feedback information based on the analyzed weight distribution information; and outputting, by a communication device, feedback information to an output device to output the feedback information to the subject, wherein the feedback information is output by the communication device to the output device so as to enable the output device to output the feedback information to the subject.

* * * * *